United States Patent [19]
Olson et al.

[11] Patent Number: 6,029,085
[45] Date of Patent: Feb. 22, 2000

[54] CHARGING AND SAFETY CONTROL FOR AUTOMATED EXTERNAL DEFIBRILLATOR AND METHOD

[75] Inventors: Kenneth F. Olson, Edina; Byron L. Gilman, Minnetonka, both of Minn.

[73] Assignee: SurVivaLink Corporation, Minneapolis, Minn.

[21] Appl. No.: 09/057,277

[22] Filed: Apr. 8, 1998

Related U.S. Application Data

[60] Provisional application No. 60/043,746, Apr. 9, 1997.

[51] Int. Cl.⁷ .................................................... A61N 1/39
[52] U.S. Cl. .................................................. 607/5; 607/63
[58] Field of Search ................................ 607/5, 63, 6, 8, 607/7

[56] References Cited

U.S. PATENT DOCUMENTS

| | | |
|---|---|---|
| 4,504,773 | 3/1985 | Suzuki et al. ................................ 607/5 |
| 4,785,812 | 11/1988 | Pihl et al. . |
| 5,179,945 | 1/1993 | Van Hofwegen et al. .................. 607/5 |
| 5,191,884 | 3/1993 | Gilli et al. .................................... 607/5 |
| 5,275,158 | 1/1994 | Lopin . |
| 5,391,187 | 2/1995 | Freeman ....................................... 607/5 |
| 5,395,394 | 3/1995 | Cameron ....................................... 607/5 |
| 5,405,361 | 4/1995 | Persson . |
| 5,439,481 | 8/1995 | Adams ........................................... 607/5 |
| 5,484,452 | 1/1996 | Persson . |
| 5,554,175 | 9/1996 | Alferness ....................................... 607/5 |
| 5,601,610 | 2/1997 | Persson . |

*Primary Examiner*—Kennedy J. Schaetzle
*Attorney, Agent, or Firm*—Patterson & Keough, P.A.

[57] ABSTRACT

A fail-safe safety circuit for a portable automated external defibrillator allows earlier charging of capacitors. In turn, the earlier charging of the capacitors allows quicker release of a defibrillation shock than prior art method of automatically detecting the appropriateness of administering a defibrillation shock and subsequently preparing the shock.

16 Claims, 2 Drawing Sheets

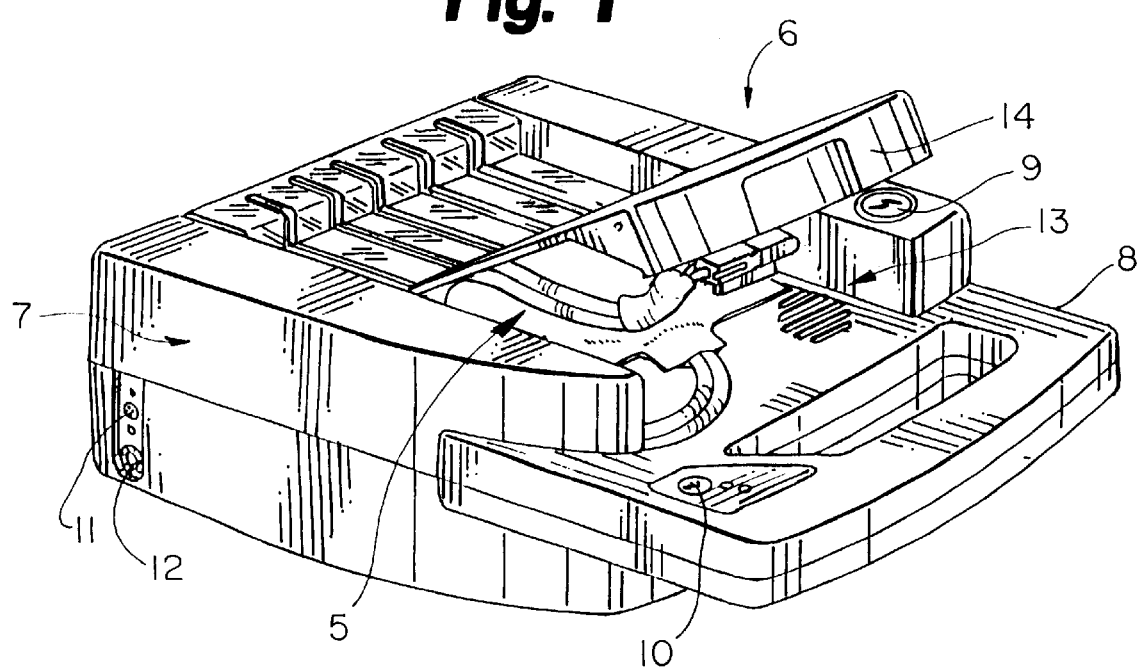

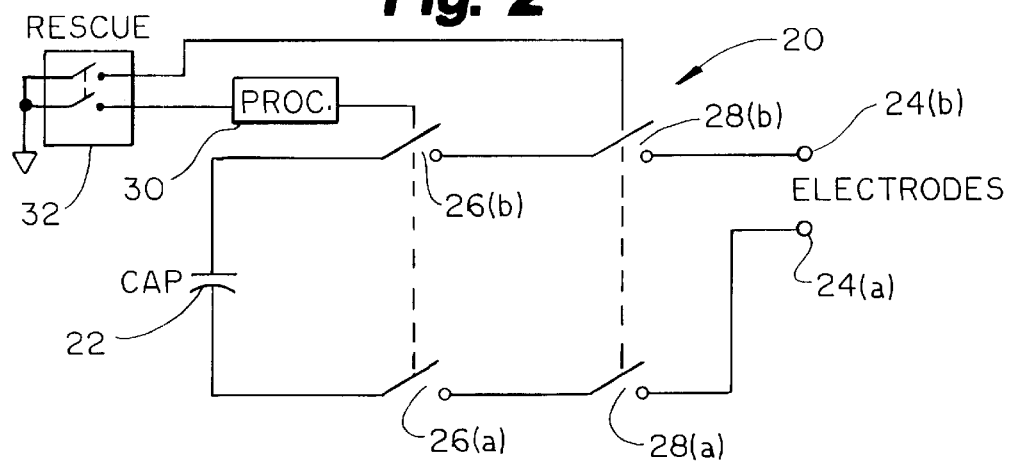
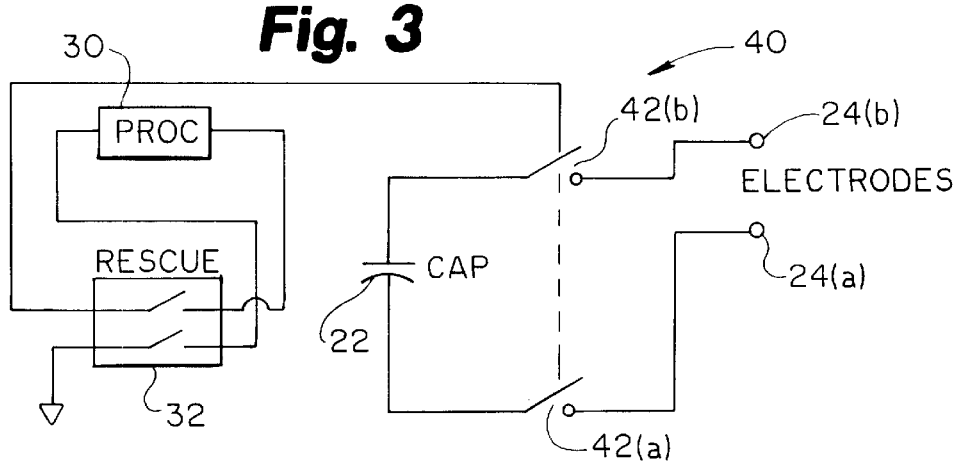
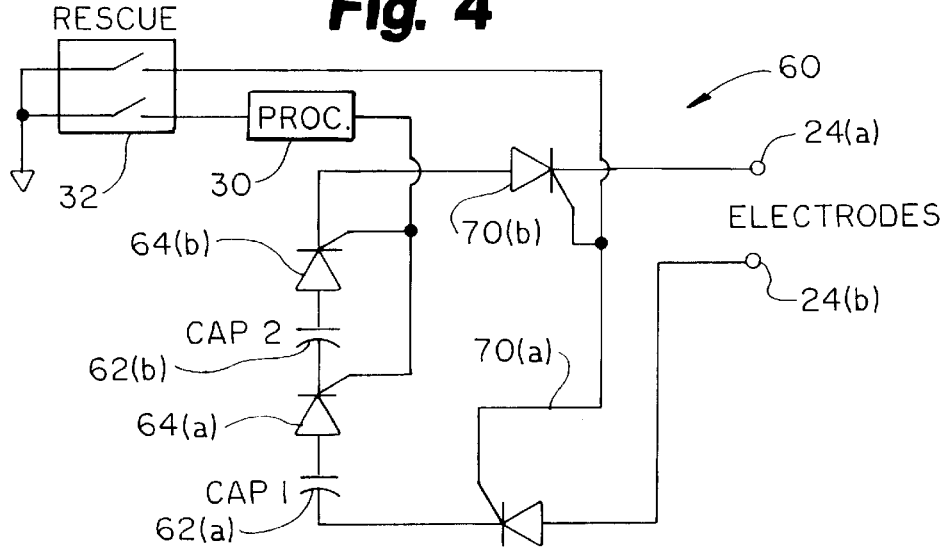

CHARGING AND SAFETY CONTROL FOR AUTOMATED EXTERNAL DEFIBRILLATOR AND METHOD

RELATED APPLICATION

The present invention is related to U.S. Provisional Patent Application Serial No. 60/043,746, filed Apr. 9, 1997, the content of which is herein incorporated by reference, and priority to which is claimed according to 35 U.S.C. § 119(e).

BACKGROUND OF THE INVENTION

The present invention relates to external defibrillators and, in particular, relates to charging and safety devices for automated external defibrillators, as well as control methods for improving the safety, efficiency, and effectiveness of external defibrillators.

Under normal circumstances, the heart functions as a pump to perfuse blood throughout the body. The pump rhythm associated with effective pumping is termed normal sinus rhythm. In certain individuals, the heart ceases to function effectively as a pump and shifts to an ineffective rhythm, termed ventricular fibrillation. Ventricular fibrillation is a non-perfusing pumping rhythm and cannot sustain life. However, it is well known that a high-energy electrical shock delivered to the chest cavity can convert ventricular fibrillation to normal sinus rhythm. This activity is termed defibrillation.

Time is a critical factor in the effectiveness of the administration of defibrillation. Specifically, after the onset of ventricular fibrillation, patient survivability decreases by about ten percent for each minute of delay until the administration of a defibrillation shock.

Emergency first aid and medical personnel are taught to consider a "Chain of Survival" model for emergencies of this type. The chain model has four critical links:

(1) Summoning emergency medical assistance by telephone by dialing "911";
(2) Cardio pulmonary resuscitation "CPR" to provide oxygen and circulation;
(3) Defibrillation to restore a pumping rhythm; and
(4) Advanced cardiac life support.

Of these four links, merely delaying any one of the associated activities significantly decreases the patient's chances of surviving. Therefore, it is apparent that there is a significant advantage to a patient when a portable defibrillator can promptly arrive on the scene and very shortly thereafter deliver a defibrillation shock to the patient.

Defibrillation has some risks involved. A defibrillation shock can be highly dangerous. Specifically, a person with a normal functioning heart producing normal sinus rhythm has a roughly ten percent chance of having that cardiac rhythm converted to ventricular fibrillation as a result of a defibrillation shock. For this reason, it is important that the defibrillation electrical shock only be administered to those patients truly experiencing ventricular fibrillation and not to patients having been misdiagnosed nor to emergency medical personnel. To distinguish such circumstances, many portable defibrillators are now "automated" which means that they include a diagnostic monitor and analysis system which can gain information about the patient by reviewing the electrical signals the patients heart is producing once the patient's chest has been fitted with defibrillation electrodes. Further, an acceptable range of impedance across the chest is observed as an indication that the electrodes are properly fitted and achieving acceptable contact with the intended patient. Clearly, a loose electrode is a potential hazard to any emergency personnel who might inadvertently receive the electrical shock. This automatic monitoring and analysis stage takes from about 9 to 14 seconds.

For safety reasons, only after an appropriate monitoring signal has been identified, do prior art defibrillators begin to charge their capacitors to generate and temporarily store a defibrillation electrical shock. This takes about 9 to 15 seconds. Thus, once the electrodes are properly fitted upon a patient, from about 20 to 30 seconds must pass before a defibrillation shock can be administered.

It can therefore be well appreciated that there exists a need for better safety arrangements as well as methods of reducing the 20 to 30 second delay between electrode fitting and delivery of a defibrillation shock necessitated by the methodology employed by prior art automated external defibrillators. The present invention, as explain below, addresses the safety and delay problems.

SUMMARY OF THE INVENTION

The present invention recognizes that in the field of automated external defibrillators, new safety mechanisms allow advantages in reducing delay while simultaneously improving safety. Further, the present invention recognizes that new methodology and the devices reflective of the new methodology in automated portable external defibrillators have several previously unappreciated advantages.

The present invention, in a first embodiment, is an automated external defibrillator. The automated external defibrillator includes at least five parts. First, it includes a means for electrical interconnection to an electrical power supply. Second, it includes a charging circuit, connected to the means for electrical interconnection, for preparing and temporarily storing a defibrillation shock. Third, it includes a manually actuated trigger switch mechanism for generating a defibrillation shock release request signal.

Fourth, the first embodiment also includes monitoring and analysis means for pre-qualifying release of a defibrillation shock in response to the defibrillation shock release request signal from the trigger switch mechanism. Fifth, it includes a safety switch mechanism, separately responsive to the defibrillation shock release request signal, for connecting a pre-qualified release of a defibrillation shock to patient electrode terminals.

In one embodiment, the manually actuated trigger switch is a single pole switch providing a single defibrillation shock release request signal for response from both the monitoring and analysis means and from the safety switch mechanism. In another embodiment, the manually actuated trigger switch is a double pole switch providing a first defibrillation shock release request signal to the monitoring and analysis means and a second, separate defibrillation shock release request signal to the safety switch mechanism. The monitoring and analysis means may be responsive to a signal generated by a closed circuit at the manually operated trigger switch. Alternatively, the monitoring and analysis means is responsive to a signal generated by a change of state of circuit closure at the manually operated trigger switch.

In one preferred embodiment, the charging circuit comprises a plurality of capacitors, connected in series and controlled by solid state relays. Desirably, such an embodiment avoids the need for high energy type switches. Even more preferable, the safety switch mechanism is also a solid state relay. The automated portable external defibrillator may desirably also include an electrical power supply.

Portability and ease of use are facilitated when the electrical power supply is a battery. With respect to the automated aspect of the invention, the monitoring and analysis means pre-qualifies a defibrillation shock release based upon at least one monitored factor selected from (1) acceptable impedance between the patient electrode terminals and (2) identification or detection of a cardiac rhythm in a potential patient (i.e. one suspected of experiencing ventricular fibrillation) predefined, in an algorithm, as indicative of ventricular fibrillation. Most preferably, both of these factors are required to pre-qualify a release of a defibrillation shock.

In another embodiment, the automated external defibrillator includes: (1) means for electrical interconnection to an electrical power supply; (2) a charging circuit, connected to the means for electrical interconnection, for preparing and temporarily storing a defibrillation shock; (3) a manually actuated double pole trigger switch mechanism for generating a defibrillation shock release request signal; (4) a safety switch mechanism, responsive to the defibrillation shock release request signal, for connecting a defibrillation shock to patient electrode terminals; and (5) monitoring and analysis means pre-qualifying the generation of the defibrillation shock release request signal.

In another embodiment, an automated external defibrillator includes: (1) an electrical power supply; (2) switched means for electrical interconnection to the electrical power supply; (3) a charging circuit, connected to the switched means for electrical interconnection, for preparing and temporarily storing a defibrillation shock; (4) a manually actuated trigger switch mechanism for generating a defibrillation shock release request signal; (5) monitoring and analysis means for pre-qualifying release of a defibrillation shock in response to the defibrillation shock release request signal from the trigger switch mechanism; (6) a switch mechanism, controlled by the monitoring and analysis means, for releasing a defibrillation shock; and (7) patient electrode terminals for connection and conveyance of a released defibrillation shock. In this embodiment, it is preferred that the switched means for electrical interconnection of the charging circuit is independent of pre-qualification activity of the monitoring and analysis means. In this embodiment, it is also preferred if the defibrillator includes a main power switch for connecting and disconnecting the defibrillator to an electrical power supply and wherein the switched means for electrical interconnection connects the charging circuit to the electrical power supply automatically upon activation of the main power switch.

It is particularly desirable that the main power switch is the switched means for electrical interconnection to the charging circuit. This results in charging and storage beginning immediately upon powering up the defibrillator.

The present invention also includes a method for providing automated portable external defibrillation shocks. The method includes the steps of: (1) providing an electrical power supply, a charging circuit capable of preparing and temporarily storing a defibrillation shock, and a switched interconnection therebetween and (2) providing a monitoring and analysis circuit to automatically prevent release of a defibrillation shock in the absence of a pre-qualified situation, and a manually actuated trigger switch mechanism to request a pre-qualified defibrillation shock release by the monitoring and analysis circuit. In this method, the step of activating the switched interconnection to begin preparing and storing a defibrillation shock is present as well as the step of (4) manually actuating the trigger switch mechanism to request the monitoring and analysis circuit to release a pre-qualified defibrillation shock. It is an important part of the inventive method that the fourth step occur subsequent to activating the switched interconnection.

In another method of this invention, an automated external defibrillation shock is provided from the steps of (1) providing an electrical power supply interconnected to a charging circuit capable of preparing and temporarily storing a defibrillation shock; (2) providing a monitoring and analysis circuit to automatically prevent release of a defibrillation shock in the absence of a pre-qualified situation, and a manually actuated trigger switch mechanism to request a pre-qualified defibrillation shock release by the monitoring and analysis circuit; (3) manually actuating the trigger switch mechanism to request the monitoring and analysis circuit to release a pre-qualified defibrillation shock; (4) providing a safety switch mechanism, separately responsive to the trigger switch mechanism, to connect the pre-qualified defibrillation shock to patient electrode terminals, thereby separately assuring that the trigger switch mechanism was manually actuated.

BRIEF DESCRIPTION OF THE DRAWINGS

FIG. 1 is a perspective view of an automated external defibrillator (AED) with a pair of electrodes attached thereto.

FIG. 2 is a schematic of the present invention in a first embodiment;

FIG. 3 is a schematic of a second embodiment; and

FIG. 4 is a schematic of another embodiment of the invention as applied to a Persson circuit.

DETAILED DESCRIPTION OF THE DRAWINGS

The present invention is an automated external defibrillator (AED) having charging and safety devices and control methods for improving the safety, efficiency and effectiveness of external defibrillators.

FIG. 1 illustrates a pair of electrodes 5 connected to an AED 6. As can be seen in FIG. 1, defibrillator 6 includes a plastic case 7 with a carrying handle 8 on the top portion. An illuminable rescue switch 9, visual maintenance indicator 10, data communication port 11 and charging port 12 are located on the outside of case 7 for easy access by an operator. Case 7 also includes an electrode compartment 13. Electrode compartment 13 is enclosed by a lid 14.

A device of the present invention is schematically represented in FIG. 2 at 20. The device 20 includes a capacitor 22 which is charged from an electrical power supply, such as a battery (not shown). The capacitor 22, when charged, can be connected to patient electrode terminals 24(a) and 24(b), leading to patient electrodes (not shown) which desirably are fitted to the chest of a patient. The circuitry between the capacitor 22 and the patient electrode terminals 24(a) and 24(b) also contains switches 26(a) and 26(b) and switches 28(a) and 28(b) all of which must be closed to allow the defibrillation shock to be delivered. Switches 26(a) and 26(b) are under control of processor 30.

Processor 30 functions to receive monitoring signals, analyze the signals and if appropriate, close switches 26(a) and 26(b). Signals which are monitored preferably include impedance between electrodes connected to terminals 24(a) and 24(b) and fitted to a patient's chest. The acceptable and appropriate impedance is within the range which should be observable across a patient's chest cavity. Only when the impedance is within preset parameters does the processor 30 allow switches 26(a) and 26(b) to be closed. Processor 30 also monitors and analyses the patient's cardiac electrical output. Only if the monitored cardiac signal, also preferably received from electrodes connected to patient electrode terminals 24(a) and 24(b), is identified as a ventricular fibrillation condition, does the processor 30 allow the switches 26(a) and 26(b) to be closed.

The processor 30 is in communication with a manual trigger switch or "rescue switch" 32. The rescue switch 32 is manually actuated by rescue personnel to signal the processor 30 to release and deliver a defibrillation shock if the processor's criterion for release and delivery have been met. If effect, the processor serves to control a pre-qualification of release of a defibrillation shock.

The rescue switch 32 also independently closes switches 28(a) and 28(b) to allow the shock to be released. This independent closure serves as a significant safety check against inadvertent shock delivery which might result from a malfunction at the processor 30. In effect, the independent closure serves as a fail safe device to assure that an emergency medical operator has indeed requested that a defibrillation shock be delivered if the processor's pre-qualification criterion have been met.

As schematically shown in FIG. 3, in another embodiment 40 of the present invention the processor 30 is connected in series with the rescue switch 32 to control a safety switch mechanism 42(a) and 42(b). As depicted in FIG. 3, in this embodiment, the rescue switch 32 is a double pole switch. Further, the rescue switch 32 is connected such that an electrical signal requesting release of a pre-qualified defibrillation shock by closure of the safety switch mechanism 42(a) and 42(b) must past through both the poles of the rescue switch 32 and that the signal connection between the double poles must also pass the processor 30. Only if the processor has pre-qualified a defibrillation shock release may the signal continue from the rescue switch 32 to close the safety switch 42(a) and 42(b). This particular embodiment 40, although useful, is somewhat less preferred because it lacks the redundancy, and therefore the increased safety and reliability of two separate switch 26(a) and 26(b) and 28(a) and 28(b) present in the depiction of FIG. 2. That is, should a signal to close the switch 42(a) and 42(b) be generated erroneously or the switch 42(a) and 42(b) fail and erroneously close, no additional safety switch in the embodiment 40 is present to prevent an unwanted defibrillation shock from being issued.

As schematically shown in FIG. 4, the present invention can also be used in a modification of the teachings of Persson in U.S. Pat. No. 5,405,361, the entire disclosure of which is hereby incorporated by reference. Persson disclosed a distributed switching scheme which uses multiple capacitors and Silicon Controlled Rectifiers (SCRs) or Field Effect Transistors (FETs) or equivalents to deliver a defibrillation shock to a patient. The Persson circuit, as modified by the present invention, is schematically shown at 60. The circuit includes multiple capacitors 62(a) and 62(b) each controlled by an SCR 64(a) and 64(b) and arranged in series. The SCRs 64(a) and 64(b) are controlled by a signal from the rescue switch 32 which must pass processor 68 before allowing a shock to be released from the capacitors 62(a) and 62(b). Only if the processor pre-qualifies a release, according to analysis of monitored information, may the request signal trigger the SCRs 64(a) and 64(b). Additionally, a separate signal is conveyed to a second safety switch mechanism involving SCRs 70(a) and 70(b). Only if the rescue switch 32 has been manually actuated are SCRs 70(a) and 70(b) closed to allow passage of the defibrillation shock to the patient electrode terminals 24(a) and 24(b). Note also that the capacitors in this arrangement may be charged in parallel which can either save time or allow the use of smaller lighter components or both.

The provision of additional safety controls to prevent the inadvertent release of a defibrillation shock reduces the need for the prior art method of sequential charging of the capacitors of the charging circuit, only after the completion of monitoring and analysis by the processor. Instead, the charging system may begin simultaneously with the monitoring and analysis function of the processor. Preferably, the charging may begin in advance of the processor function. This may be as early as possible, such as by initiating charging when the defibrillator is initially powered up. Several advantages are available from this approach. First, the delay of waiting for the charge system may be reduced or even eliminated, thereby allowing a defibrillation shock to be dispensed to a patient earlier. As well accepted, seconds are precious at this stage in a coronary emergency. Alternatively, the size of batteries and other components of a defibrillator may be reduced making the equipment lighter and quicker to deploy.

Because numerous modifications may be made of this invention without departing from the spirit thereof, the scope of the invention is not to be limited to the single embodiment illustrated and described. Rather, the scope of the invention is to be determined by appended claims and their equivalents.

What is claimed is:

1. An automated external defibrillator comprising:
    a charging circuit for preparing and temporarily storing a defibrillation shock;
    a manually actuated trigger switch mechanism for generating a defibrillation shock release request signal;
    monitoring and analysis means operably communicatively coupled to the trigger switch mechanism for pre-qualifying release of a defibrillation shock in response to the defibrillation shock release request signal from the trigger switch mechanism; and
    a safety switch mechanism operably communicatively coupled to the trigger switch mechanism, separately responsive to the defibrillation shock release request signal from the monitoring and analysis means, for connecting a pre-qualified release of a defibrillation shock to patient electrode terminals.

2. The automated external defibrillator of claim 1, wherein the manually actuated trigger switch is a single pole switch providing a single defibrillation shock release request signal for response from both the monitoring and analysis circuit and from the safety switch.

3. The automated external defibrillator of claim 1, wherein the manually actuated trigger switch is a double pole switch providing a first defibrillation shock release request signal to the monitoring and analysis circuit and a second, separate defibrillation shock release request signal to the safety switch.

4. The automated external defibrillator of claim 1 wherein the monitoring and analysis means is responsive to the defibrillation shock release signal produced by manually closing the trigger switch.

5. The automated external defibrillator of claim 1, wherein the monitoring and analysis circuit is responsive to a signal generated by a change of state of circuit closure at the manually operated trigger switch.

6. The automated external defibrillator of claim 1 wherein the charging circuit comprises a plurality of capacitors, connected in series and controllable by solid state relays.

7. The automated external defibrillator of claim 6, wherein the safety switch includes a solid state relay.

8. The automated external defibrillator of claim 1 and wherein the monitoring and analysis means pre-qualifies a defibrillation shock release based upon at least one monitored factor selected from the group consisting of:

acceptable impedance between the patient electrode terminals; and detection of a cardiac rhythm predefined as indicative of ventricular fibrillation.

9. An automated portable external defibrillator comprising:

a charging circuit for preparing and temporarily storing a defibrillation shock;

a manually actuated double pole trigger switch mechanism for generating a defibrillation shock release request signal; and a safety switch mechanism, responsive to the defibrillation shock release request signal, for connecting a defibrillation shock to patient electrode terminals; and monitoring and analysis means prequalifying the generation of the defibrillation shock release request signal.

10. The automated external defibrillator of claim 9 wherein the monitoring and analysis means pre-qualifies a defibrillation shock release based upon at least one monitored factor selected from the group consisting of:

acceptable impedance between the patient electrode terminals, and detection of a cardiac rhythm predefined as indicative of ventricular fibrillation.

11. An automated external defibrillator comprising:

switch means for electrical interconnection to the electrical power supply;

a charging circuit, connected to the switch means for electrical interconnection, for preparing and temporarily storing a defibrillation shock;

a manually actuated trigger switch mechanism for generating a defibrillation shock release request signal;

monitoring and analysis means for pre-qualifying release of a defibrillation shock in response to the defibrillation shock release request signal from the trigger switch mechanism;

a switch mechanism, controlled by the monitoring and analysis means, for releasing a defibrillation shock; and patient electrode terminals for connection and conveyance of a released defibrillation shock.

12. The automated external defibrillator of claim 11 and wherein the switch means for electrical interconnection of the power supply is independent of pre-qualification activity of the monitoring and analysis means.

13. A method for providing automated external defibrillation shocks, comprising the steps of:

providing an electrical power supply, a charging circuit capable of preparing and temporarily storing a defibrillation shock, and a switched interconnection therebetween;

providing a monitoring and analysis circuit to automatically prevent release of a defibrillation shock in the absence of a pre-qualified situation, and a manually actuated trigger switch to request a pre-qualified defibrillation shock release by the monitoring and analysis circuit;

activating the switched interconnection to begin preparing and storing a defibrillation shock; and subsequent to activating the switched interconnection, manually actuating the trigger switch to request the monitoring and analysis circuit to release a pre-qualified defibrillation shock.

14. A method for providing automated external defibrillation shocks, comprising the steps of:

providing a monitoring and analysis circuit to automatically prevent release of a defibrillation shock in the absence of a pre-qualified situation, and a manually actuated trigger switch mechanism to request a pre-qualified defibrillation shock release by the monitoring and analysis circuit;

manually actuating the trigger switch mechanism to request the monitoring and analysis circuit to release a pre-qualified defibrillation shock;

providing a safety switch mechanism, separately responsive to the trigger switch mechanism from the monitoring and analysis circuit, to connect the pre-qualified defibrillation shock to patient electrode terminals, thereby separately assuring that the trigger switch mechanism was manually actuated.

15. A method for providing a defibrillation shock using an automated external defibrillator (AED) having AED circuitry including an electrical power supply interconnected to a charging circuit capable of preparing and temporarily storing a defibrillation shock, a pair of electrodes connected to the charging circuit, a processor for controlling operation of the AED, an analysis circuit connected to the processor, and a trigger switch operably coupled to the AED circuitry for initiating generation of a defibrillating shock, the method including the steps of:

turning the AED on;

activating the charging circuit to prepare and store a defibrillation shock;

instigating the analysis circuit after the charging circuit has been activated, and generating the defibrillating shock, deliverable to a patient.

16. A method for providing a defibrillation shock using an automated external defibrillator having AED circuitry including an electrical power supply interconnected to a charging circuit capable of preparing and temporarily storing a defibrillation shock, a pair of electrodes connected to the charging circuit, a processor for controlling operation of the AED, an analysis circuit connected to the processor, and a trigger switch operably coupled to the AED circuitry for initiating generation of a defibrillating shock, the method including the steps of:

turning the AED on;

activating the charging circuit to prepare and store a defibrillation shock;

instigating the analysis circuit simultaneously to the actuation of the charging circuit, and generating the defibrillating shock, deliverable to a patient.

* * * * *